United States Patent
Farmen et al.

(10) Patent No.: US 9,885,702 B1
(45) Date of Patent: *Feb. 6, 2018

(54) ISOTOPICALLY-LABELED SOLVENTS AND THE USE OF SAME IN TESTING E-CIGARETTES

(71) Applicant: Celerion, Inc., Lincoln, NE (US)

(72) Inventors: Raymond H. Farmen, Lincoln, NE (US); Christine Kafonek, Lincoln, NE (US)

(73) Assignee: Celerion, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/473,033

(22) Filed: Mar. 29, 2017

Related U.S. Application Data (63) Continuation-in-part of application No. 14/481,394, filed on Sep. 9, 2014, now Pat. No. 9,645,134.

(60) Provisional application No. 61/875,650, filed on Sep. 9, 2013, provisional application No. 61/875,647, filed on Sep. 9, 2013.

(51) Int. Cl.

| | |
|---|---|
| *A61K 51/00* | (2006.01) |
| *A61M 36/14* | (2006.01) |
| *G01N 33/49* | (2006.01) |
| *G01N 33/487* | (2006.01) |
| *G01N 33/493* | (2006.01) |
| *G01N 33/58* | (2006.01) |
| *A24B 15/16* | (2006.01) |
| *A24F 47/00* | (2006.01) |

(52) U.S. Cl.
CPC ........... *G01N 33/49* (2013.01); *A24B 15/167* (2016.11); *A24F 47/008* (2013.01); *G01N 33/487* (2013.01); *G01N 33/493* (2013.01); *G01N 33/58* (2013.01); *A61K 2123/00* (2013.01); *G01N 2458/15* (2013.01)

(58) Field of Classification Search
None
See application file for complete search history.

(56) References Cited

U.S. PATENT DOCUMENTS

| | | | |
|---|---|---|---|
| 4,140,003 | A | 2/1979 | Pillsbury, Jr. et al. |
| 4,900,664 | A | 2/1990 | Israel et al. |
| 2006/0018793 | A1 | 1/2006 | Hashiba et al. |
| 2008/0145947 | A1 | 6/2008 | Boga et al. |
| 2010/0075431 | A1 | 3/2010 | Zhou et al. |
| 2012/0028360 | A1 | 2/2012 | Tordoff |
| 2013/0081642 | A1 | 4/2013 | Safari |

FOREIGN PATENT DOCUMENTS

| | | |
|---|---|---|
| WO | 1998039652 A1 | 9/1998 |

OTHER PUBLICATIONS

Polosa et al., "Effect of an electronic nicotine delivery device (e-Cigarette) on smoking reduction and cessation: a prospective 6-month pilot study," http://www.biomedcentral.com/1471-2458/11/786, BMC Public Health, published Oct. 11, 2011.

Polosa et al., Figure 1, BMC Public Health, http://www.biomedcentral.com/1471-2458/11/786/figure/F1, BMC Public Health 2011 11:786 doi:10.1186/1471-2458-11-786, 2011.

Polosa et al., Figure 2, BMC Public Health 2011 11:786 doi:10.1186/1471-2458-11-786, http://www.biomedcentral.com/1471-2458/11/786/figure/F2, 2011.

Polosa et al., Figure 3, BMC Public Health, http://www.biomedcentral.com/content/figures/1471-2458-11-786-3-jpg, 2011.

Bullen et al., "Effect of an electronic nicotine delivery device (e cigarette) on desire to smoke and withdrawal, user preferences and nicotine delivery: randomised cross-over trial," Tob Control 2010 19: 98-103 doi: 10.1136/tc.2009.031567, Apr. 2010.

Molander et al., "Pharmacokinetic investigation of a nicotine sublingual tablet," http://www.ncbi.nlm.nih.gov/pubmed/11294371, 2001, Eur J Clin Pharmacol. Jan.-Feb. 2001—PubMed—NCBI.

Digard et al., "Determination of Nicotine Absorption from Multiple Tobacco Products and Nicotine Gum," Nicotine Tob Res (2012) doi: 10.1093/ntr/nts123, http://ntr.oxfordjournals.org/content/early/2012/05/13/ntr.nts123.full, first published online: May 18, 2012.

(Continued)

*Primary Examiner* — Michael G Hartley
*Assistant Examiner* — Melissa J Perreira
(74) *Attorney, Agent, or Firm* — Crawford Maunu PLLC (57) ABSTRACT

Isotopically-labeled species of propylene glycol and glycerol are provided as solvents for use in electronic nicotine delivery systems (e.g., as disposed in a cartridge in an e-cigarette). The isotopically-labeled species are distinguishable from the non-isotopically-labeled species (e.g., by mass spectrometry). Thus, methods are provided for the measurement of the quantity of solvent or of a solvent heating by-product (e.g., formaldehyde, acetaldehyde), or of a metabolite of the drug, delivered to a user by analysis of blood samples taken subsequent to dosing by use of the electronic nicotine delivery system. An example of an isotopically-labeled species of propylene glycol for use in such measurement methods is $[^{13}C]_3H_8O_2$. A clinical study of e-cigarettes loaded with this isotopically-labeled species resulted in the following blood plasma concentration profiles in "vaping" subjects.

19 Claims, 3 Drawing Sheets

(56) References Cited

OTHER PUBLICATIONS

Eissenberg, "Electronic nicotine delivery devices: ineffective nicotine delivery and craving suppression after acute administration," doi: 10.1136/tc.2009.033498, http://www.ncbi.nlm.nih.gov/pmc/articles/PMC3208854/, Tob. Control. Feb. 2010; 19(1): 87-88, doi: 10.1136/tc.2009.033498.

"Coresta Recommended Method No. 22—Routine analystical cigarette-smoking machine specifications, definitions, and standard conditions," Aug. 1991.

"Coresta Recommended Method No. 7—Determination of nicotine in the mainstream smoke of cigarettes by gas chromatographic analysis," Aug. 1991.

"Acetaldehyde Reference Exposure Levels, (ethanal; acetic aldehyde; acetylaldehyde; ethylaldehyde; diethylacetyl)", Draft TSD for Noncancer RELs, SRP4, Sep. 2008.

Vansickel et al. (Cancer Epidemiol. Biomarkers Prey. 2010, 19, 1945-1953).

McAuley et al. (Inhalation Toxicol. 2012, 24, 850-857).

Emsley et al. (J. Chem. Soc. Faraday II, 1975, 7, 586-595).

Bergstrom et al. (Cline. Pharmacol. Ther. 1995, 57, 309-317).

http://www.news-medical.net/news/20091104/Propylene-glycol-in-e-cigareftes-might-keep-us-healthy-says-researchers.aspx, Nov. 4, 2009.

Federal Register 2004, 69, 34937-34944.

ISOTOPICALLY-LABELED SOLVENTS AND THE USE OF SAME IN TESTING E-CIGARETTES

CROSS-REFERENCE TO RELATED APPLICATIONS

This application is a continuation-in-part of U.S. application Ser. No. 14/481,394, filed on Sep. 9, 2014, which in turn claims priority to U.S. provisional application Nos. 61/875,647 and 61/875,650, both filed on Sep. 9, 2013. The contents of each of the foregoing patent applications is incorporated by reference herein in its entirety for any purpose whatsoever.

BACKGROUND

Electronic nicotine delivery systems ("ENDS"), often referred to as electronic cigarettes or e-cigarettes, are rapidly becoming a popular alternative to cigarette smoking worldwide. ENDS typically consist of a battery, heating component, and a cartridge or tank containing tobacco-derived nicotine in a solution composed of glycerin and/or propylene glycol ("PG"), and flavorings. Upon activation, the heating element heats the solution and the consumer inhales the resulting vapor. Two general types of ENDS exist in the market currently. The "cig-alikes" are similar in appearance to conventional cigarettes and are largely used in the form purchased. "VTMs" (vapors-tanks-mods) are typically larger in size, stronger and interchangeable batteries, and allow subjects to fill the device with solutions customized in flavor and nicotine concentration.

The inventors are unaware of any well-controlled studies published to date that have been able to attribute a specific level of PG exposure from the use of ENDS products. One limiting factor in this assessment is that PG is commonly consumed in foods and beverages, making it impossible to definitively differentiate PG exposure from multiple sources. To overcome this limitation, PG can be synthesized with a carbon-heavy atom (C13, non-radioactive stable isotope) and safely administered to subjects using commercial vaporizer products. Using LC/MS/MS methods, the resulting PG exposure can then be definitively linked to use of the device not only by those who use the product, but also by individuals who are exposed to the second-hand vapor.

PG is widely used in the pharmaceutical, cosmetic, and food industries as a preservative, solvent, and humectant, and is generally regarded as safe by the United States Food and Drug Administration. PG is metabolized in the liver by alcohol dehydrogenase to lactic acid and then pyruvate, and ultimately carbon dioxide and water, while approximately 45% is excreted by the kidneys unchanged or as the glucuronide conjugate. The half-life of PG is approximately 4 hours. The average daily intake of PG from food products in the US is estimated to be approximately 2400 mg. A wide variety of foods contain PG, including ice cream, cake mixes and frosting, cookies, candy, salad dressing and soft drinks.

Electronic nicotine delivery systems essentially eliminate the inhalation of combustion products of conventional cigarettes by providing a tobacco extract or similar material containing nicotine dissolved in a solvent, usually propylene glycol or glycerin. This material is then heated in the e-cigarette, typically by induction heating, which causes the solvent and nicotine to vaporize. The resulting vapor is then inhaled which delivers the nicotine to the user. In the process of heating the solvent some of the solvent is converted to formaldehyde and acetaldehyde, which is also inhaled.

SUMMARY OF THE INVENTION

The present invention is generally directed to isotopically-labelled solvents and their uses in methods of measuring the quantities of particular materials delivered to users of e-cigarettes.

In a first embodiment, the invention is directed to an isotopically-labeled species of propylene glycol selected from the group consisting of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65 and B66 and the 1-3 isomers thereof.

In a second embodiment, the invention is directed to the isotopically-labeled species of propylene glycol according to the first embodiment that is $[^{13}C]_3H_8O_2$ (A3).

In a third embodiment, the invention is directed to a purified form of the isotopically-labeled species of propylene glycol according to the first embodiment that is $[^{13}C]_3H_8O_2$ (A3) and is at least 95 wt. percent pure.

In a fourth embodiment, the invention is directed to the isotopically-labeled species of propylene glycol according to the first embodiment that is selected from the group consisting of $[^{13}C]_3[^2H]_2H_6O_2$, $[^{13}C]_3[^2H]_3H_5O_2$, $[^{13}C]_3[^2H]_4H_4O_2$, $[^{13}C]_3[^2H]_5H_3O_2$ and $[^{13}C]_3[^2H]_6H_2O_2$ (A29-A33).

In a fifth embodiment, the invention is directed to an isotopically-labeled species of glycerol selected from the group consisting of C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88 and D89.

In a sixth embodiment, the invention is directed to the isotopically-labeled species of glycerol according to the fifth embodiment that is $[^{13}C]_3[^2H]_5H_3O_3$ (C32).

In a seventh embodiment, the invention is directed to the isotopically-labeled species of glycerol according to the fifth embodiment that is selected from the group consisting of $[^{13}C]_3H_8O_3$, $[^{13}C]_3[^2H]H_7O_3$, and $[^{13}C]_3[^2H]_2H_6O_3$, (C3-C5).

In an eighth embodiment, the invention is directed to an e-cigarette cartridge loaded with a liquid comprising nicotine dissolved in a pre-determined quantity of a solvent comprising an isotopically-labelled species of propylene glycol according to the first embodiment.

In a ninth embodiment, the invention is directed to the e-cigarette cartridge according to the eighth embodiment, wherein said isotopically-labeled species of propylene glycol is $[^{13}C]_3H_8O_2$ (A3).

In a tenth embodiment, the invention is directed to the e-cigarette cartridge according to the eighth embodiment, wherein the concentration of said nicotine in said solvent is between about 0.3 and about 4.0 v/v %.

In an eleventh embodiment, the invention is directed to an e-cigarette cartridge loaded with a liquid comprising nicotine dissolved in a pre-determined quantity of a solvent comprising an isotopically-labelled species of glycerol according to the fifth embodiment.

In a twelfth embodiment, the invention is directed to the e-cigarette cartridge according to the eleventh embodiment, wherein said isotopically-labeled species of glycerol is $[^{13}C]_3[^2H]_5H_3O_3$ (C32).

In a thirteenth embodiment, the invention is directed to a method of determining a quantity of a compound delivered to a user of an e-cigarette including providing a user with an e-cigarette including an e-cigarette cartridge loaded with a liquid that includes a predetermined quantity of solvent that includes non-radioactive isotopically labeled propylene glycol that is isotopically enriched by at least three (e.g., 3, 4, 5, 6, 7, 8, etc.) atomic mass units, dosing the user with said e-cigarette, obtaining a bodily fluid sample from the user, and determining the amount of isotopically-labeled propylene glycol in the bodily fluid by measuring the concentration of isotopically-labeled propylene glycol in the bodily fluid sample. In some embodiments, an amount of un-labeled propylene glycol can also be measured.

If desired, the liquid can further include nicotine. If desired, the concentration of said nicotine in the liquid is between about 0.3 and about 4.0 v/v %. If desired, the bodily fluid sample is a blood sample. The level of isotopically-labeled propylene glycol in the blood plasma can be measured using mass spectrometry. In further implementations, the bodily fluid sample can be a saliva sample or a urine sample, and the level of isotopically-labeled propylene glycol in the fluid sample can be measured using mass spectrometry.

In some implementations, only the carbon atoms of the propylene glycol are isotopically weighted. In other implementations, only the hydrogen atoms of the propylene glycol are isotopically weighted. In still others, only the hydrogen atoms and oxygen atoms of the propylene glycol are isotopically weighted. If desired, the carbon atoms, hydrogen atoms and oxygen atoms of the propylene glycol are each isotopically weighted. Alternatively, only the carbon atoms and oxygen atoms of the propylene glycol are isotopically weighted. In some embodiments, only the hydrogen atoms and carbon atoms of the propylene glycol are isotopically weighted.

The disclosure further provides an e-cigarette loaded with a mixture including propylene glycol that is isotopically enriched by at least three atomic mass units, which can further includes nicotine, for example, in a concentration between about 0.3 and about 4.0 v/v %. The disclosure further provides a cartridge for an e-cigarette loaded with a mixture including propylene glycol that is isotopically enriched by at least three atomic mass units.

Those of skill in the art will recognize that other aspects of the invention will become manifest in view of the description.

DESCRIPTION

The inventors have come to appreciate that it is advantageous to know the biological levels of the inhaled solvent that result from the use of e-cigarettes. However, this can be difficult as both propylene glycol and glycerol are ubiquitous or endogenous compounds and are measurable in all blood plasma of all subjects either from environmental exposure (propylene glycol) or as byproducts of normal metabolic pathways (glycerol).

Accordingly, in a first aspect, a method, system and consumable item are provided for detecting the presence of solvents from e-cigarettes delivered to a user. This can be accomplished by including a tracer, such as a nonradioactive, stable isotopically-labeled solvent, in a cartridge for an e-cigarette, in order to permit detection of the compound after it has been absorbed or otherwise taken in by a user. Various techniques can be used to determine the amount of isotopically-labeled solvent delivered to the user's body from the e-cigarette. In one implementation, a blood sample can be taken from a user of an e-cigarette to determine the amount, for example, of isotopically-labeled solvent present in the blood sample. Alternatively, samples of other bodily fluids materials or products can also be analyzed for the presence of the isotopically-labeled solvent, including but not limited to a user's saliva, urine, mucus, stool, perspiration, and the like. In some implementations, interior bodily surfaces can be swiped to obtain bodily fluids and/or cellular material such as by swiping the interior of the user's mouth, throat, nasal passages and the like.

The isotopically-labeled solvent is most preferably non-radioactive and be isotopically enhanced by including constituent elements in the solvent molecule that are "heavy" non-radioactive isotopes of the more commonly occurring elements. The presence of the isotopically enhanced species can then be determined by way of mass spectrometry, for example, as such techniques can be used to distinguish molecules based upon their atomic mass. In some implementations, species can be synthesized using stable isotopes of hydrogen (deuterium/$^2H$), carbon ($^{13}C$), and the like. When these moieties are incorporated into the molecule the physical chemical properties of the molecule remain very much the same with the exception that the molecule weighs more. This increase in molecular mass can be detected with a mass spectrometer.

As used herein, the term "species" means the specific atomic form of the molecule (as indicated by the species formulae in Tables 2-5). "Isotopically-labeled species" means those species that incorporate one or more atoms of the heavy moieties (e.g., $^2H$, $^{13}C$). As used herein, the term "solvent" means a quantity of liquid in which the drug (e.g., nicotine) is soluble. "Isotopically-labeled solvent" means a quantity of liquid substantially comprising an isotopically-labeled species.

Thus, in one aspect, a method is provided including disposing a solvent with stable isotopes in an e-cigarette, permitting a user to smoke the e-cigarette and collecting the biofluids of the user. The biofluids can then be analyzed to determine the levels of, for example, isotopically-labeled solvent, and additional chemicals such as formaldehyde and/or acetaldehyde in the biofluids that originated from the e-cigarette. Additionally or alternatively, the unlabeled solvent, propylene glycol and, in some embodiments, glycerol, present as a result of exposure to other sources or due to normal metabolism can be measured in the biofluids. The solvent can be disposed in the e-cigarette on its own, or mixed with other compounds, such as nicotine and the like. Accordingly, the unlabeled analytes resulting from the testing can be expected to be representative of the endogenous levels of the compounds, and the isotopically-labeled analytes that are detected can be expected to be representative of the levels that came from using the e-cigarette.

In some implementations, the disclosure provides an e-cigarette, e-cigarette cartridge or e-cigarette including an e-cigarette cartridge that includes a predetermined quantity of an isotopically-labeled solvent. The isotopically-labeled solvent can be, for example, one or more isotopes of propylene glycol, as discussed herein.

Any or all of the carbon, hydrogen and oxygen in each of the propylene glycol compounds can be enhanced through the use of isotopes (e.g., $^{13}C$, $^{2}H$, $^{18}O$), Preferably, at least the carbon of any given molecule is to include $^{13}C$.

Propylene glycol (1,2-propanediol or propane-1, 2-diol) and glycerol (glycerin, propane-1, 2, 3-triol) are organic alcohols with low acute oral toxicity (LD50: 18500 mg/kg propylene glycol in rabbit and 10,000 mg/kg glycerol in rabbit). They are on the FDA list of compounds that are generally recognized as safe (GRAS) and are widely used in pharmaceutical, cosmetic, consumer product, and food industry applications. Exposure to propylene glycol and glycerol is likely to be fairly ubiquitous and possibly variable.

Isotopically-labeled propylene glycol and glycerol can be chemically distinguishable from other sources by radiometric (only for radio-isotopes) or mass spectrometric (both stable-isotopes and radio-isotopes) detection as the isotopically-labeled species would have different atomic masses than native species. Administration of compounds labeled with radioactive isotopes is complex, requiring special licenses and training due to the risks associated with exposure to radioactivity. As such, stable isotopes that are not radioactive and present no inherent health hazard can be advantageous, particularly since they are relatively rare. Deliberately enriching their abundance in a molecule, such as for example propylene glycol and/or glycerol can make them identifiable in the presence of the same molecules with a naturally occurring abundance of isotopic atoms.

In the tables below, average mass is the average atomic mass of the species with a naturally occurring abundance of isotopic atoms [H ($^{1}H$), $^{2}H$, $^{3}H$, C ($^{12}C$), $^{13}C$, $^{14}C$, O ($^{16}O$), $^{18}O$) and exact mass is the atomic mass when only atoms of the most common isotope species are present (H, C, O).

TABLE 1

| Structure | Molecular Formula | Average Mass | Exact Mass |
|---|---|---|---|
| OH<br>HO⟋⟍ | $C_3H_8O_2$ | 76.10 | 76.052430 |
| OH<br>HO⟋⟍⟋OH | $C_3H_8O_3$ | 92.09 | 92.047344 |

There are numerous possible stable isotope-labeled propylene glycol molecules, but there may be some that are more useful than others. Propylene glycol is metabolized to lactate (lactic acid anion). The use of $^{13}C_3$-propylene glycol can then potentially result in a uniformly labeled lactate molecule should analysis of lactate be desired.

1 Alcohol dehydrogenase
2 Glyoxalase I, II (d-lactic acid only)

Thus, in some embodiments, the invention is directed to the metabolites of isotopically-labeled propylene glycol ($^{13}[C]_3H_8O_2$), including lactaldehyde ($^{13}[C]_3H_5O_2$), lactic acid ($^{13}[C]_3H_5O_2$) and methylglyoxal ($^{13}[C]_3H_5O_2$), herein referenced as species G1, G2 and G3, respectively. In other embodiments, the invention is directed to the metabolites of isotopically-labeled propylene glycerol.

For mass spectrometric detection, a stable-labeled internal standard is also desirable. Labeling propylene glycol with deuterium on carbon atoms, as opposed to oxygen atoms, is most preferred. While any of the below species can be used as an e-cigarette solvent or a standard, presently preferred species are indicated. Table 2 presents the inventive isotopically-labeled species of 1-2 propylene glycol.

TABLE 2

| Species Formula | Average Enriched Mass | Species No., Comment |
|---|---|---|
| $[^{13}C]C_2H_8O_2$ | 77.10 | $A_1$ |
| $[^{13}C]_2CH_8O_2$ | 78.11 | $A_2$ |
| $[^{13}C]_3H_8O_2$ | 79.12 | $A_3$, Preferred for e-cig solvent |
| $C_3[^2H]H_7O_2$ | 77.10 | $A_4$ |
| $C_3[^2H]_2H_6O_2$ | 78.11 | $A_5$ |
| $C_3[^2H]_3H_5O_2$ | 79.12 | $A_6$ |
| $C_3[^2H]_4H_4O_2$ | 80.13 | $A_7$ |
| $C_3[^2H]_5H_3O_2$ | 81.14 | $A_8$ |
| $C_3[^2H]_6H_2O_2$ | 82.15 | $A_9$ |
| $C_3[^2H]_7HO_2$ | 83.16 | $A_{10}$ |
| $C_3[^2H]_8O_2$ | 84.16 | $A_{11}$ |
| $[^{13}C]C_2[^2H]H_7O_2$ | 78.11 | $A_{12}$ |
| $[^{13}C]C_2[^2H]_2H_6O_2$ | 79.12 | $A_{13}$ |
| $[^{13}C]C_2[^2H]_3H_5O_2$ | 80.13 | $A_{14}$ |
| $[^{13}C]C_2[^2H]_4H_4O_2$ | 81.14 | $A_{15}$ |
| $[^{13}C]C_2[^2H]_5H_3O_2$ | 82.15 | $A_{16}$ |
| $[^{13}C]C_2[^2H]_6H_2O_2$ | 83.16 | $A_{17}$ |
| $[^{13}C]C_2[^2H]_7HO_2$ | 84.16 | $A_{18}$ |
| $[^{13}C]C_2[^2H]_8O_2$ | 85.17 | $A_{19}$ |
| $[^{13}C]_2C[^2H]H_7O_2$ | 79.12 | $A_{20}$ |
| $[^{13}C]_2C[^2H]_2H_6O_2$ | 80.13 | $A_{21}$ |
| $[^{13}C]_2C[^2H]_3H_5O_2$ | 81.14 | $A_{22}$ |
| $[^{13}C]_2C[^2H]_4H_4O_2$ | 82.15 | $A_{23}$ |
| $[^{13}C]_2C[^2H]_5H_3O_2$ | 83.16 | $A_{24}$ |
| $[^{13}C]_2C[^2H]_6H_2O_2$ | 84.16 | $A_{25}$ |
| $[^{13}C]_2C[^2H]_7HO_2$ | 85.17 | $A_{26}$ |
| $[^{13}C]_2C[^2H]_8O_2$ | 86.18 | $A_{27}$ |

TABLE 2-continued

| Species Formula | Average Enriched Mass | Species No., Comment |
|---|---|---|
| $[^{13}C]_3[^2H]H_7O_2$ | 80.13 | $A_{28}$ |
| $[^{13}C]_3[^2H]_2H_6O_2$ | 81.14 | $A_{29}$, Preferred for internal standard |
| $[^{13}C]_3[^2H]_3H_5O_2$ | 82.15 | $A_{30}$, Preferred for internal standard |
| $[^{13}C]_3[^2H]_4H_4O_2$ | 83.16 | $A_{31}$, Preferred for internal standard |
| $[^{13}C]_3[^2H]_5H_3O_2$ | 84.16 | $A_{32}$, Preferred for internal standard |
| $[^{13}C]_3[^2H]_6H_2O_2$ | 85.17 | $A_{33}$, Preferred for internal standard |
| $[^{13}C]_3[^2H]_7HO_2$ | 86.18 | $A_{34}$ |
| $[^{13}C]_3[^2H]_8O_2$ | 87.19 | $A_{35}$ |

However, isotopic enrichment can also be accomplished, utilizing any of the propylene glycol species in Table 3 in the e-cigarette solvent or standard:

TABLE 3

| Species Formula | Species No., Average Enriched Mass |
|---|---|
| $[^{13}C]C_2H_8O_2$ | $B_1$, 77.10 |
| $[^{13}C]_2CH_8O_2$ | $B_2$, 78.11 |
| $[^{13}C]_3H_8O_2$ | $B_3$, 79.12 |
| $C_3[^2H]H_7O_2$ | $B_4$, 77.10 |
| $C_3[^2H]_2H_6O_2$ | $B_5$, 78.11 |
| $C_3[^2H]_3H_5O_2$ | $B_6$, 79.12 |
| $C_3[^2H]_4H_4O_2$ | $B_7$, 80.13 |
| $C_3[^2H]_5H_3O_2$ | $B_8$, 81.14 |
| $C_3[^2H]_6H_2O_2$ | $B_9$, 82.15 |
| $C_3[^2H]_7HO_2$ | $B_{10}$, 83.16 |
| $C_3[^2H]_8O_2$ | $B_{11}$, 84.16 |
| $C_3H_8[^{18}O]O$ | $B_{12}$, 78.11 |
| $C_3H_8[^{18}O]_2$ | $B_{13}$, 80.13 |
| $[^{13}C]C_2[^2H]H_7O_2$ | $B_{14}$, 78.11 |
| $[^{13}C]C_2[^2H]_2H_6O_2$ | $B_{15}$, 79.12 |
| $[^{13}C]C_2[^2H]_3H_5O_2$ | $B_{16}$, 80.13 |
| $[^{13}C]C_2[^2H]_4H_4O_2$ | $B_{17}$, 81.14 |
| $[^{13}C]C_2[^2H]_5H_3O_2$ | $B_{18}$, 82.15 |
| $[^{13}C]C_2[^2H]_6H_2O_2$ | $B_{19}$, 83.16 |
| $[^{13}C]C_2[^2H]_7HO_2$ | $B_{20}$, 84.16 |
| $[^{13}C]C_2[^2H]_8O_2$ | $B_{21}$, 85.17 |
| $[^{13}C]_2C[^2H]H_7O_2$ | $B_{23}$, 79.12 |
| $[^{13}C]_2C[^2H]_2H_6O_2$ | $B_{24}$, 80.13 |
| $[^{13}C]_2C[^2H]_3H_5O_2$ | $B_{25}$, 81.14 |
| $[^{13}C]_2C[^2H]_4H_4O_2$ | $B_{26}$, 82.15 |
| $[^{13}C]_2C[^2H]_5H_3O_2$ | $B_{27}$, 83.16 |
| $[^{13}C]_2C[^2H]_6H_2O_2$ | $B_{28}$, 84.16 |
| $[^{13}C]_2C[^2H]_7HO_2$ | $B_{29}$, 85.17 |
| $[^{13}C]_2C[^2H]_8O_2$ | $B_{30}$, 86.18 |
| $[^{13}C]_3[^2H]H_7O_2$ | $B_{31}$, 80.13 |
| $[^{13}C]_3[^2H]_2H_6O_2$ | $B_{32}$, 81.14 |
| $[^{13}C]_3[^2H]_3H_5O_2$ | $B_{33}$, 82.15 |
| $[^{13}C]_3[^2H]_4H_4O_2$ | $B_{34}$, 83.16 |
| $[^{13}C]_3[^2H]_5H_3O_2$ | $B_{35}$, 84.16 |
| $[^{13}C]_3[^2H]_6H_2O_2$ | $B_{36}$, 85.17 |
| $[^{13}C]_3[^2H]_7HO_2$ | $B_{37}$, 86.18 |
| $[^{13}C]_3[^2H]_8O_2$ | $B_{38}$, 87.19 |
| $[^{13}C]C_2H_8[^{18}O]O$ | $B_{39}$, 79.12 |
| $[^{13}C]_2CH_8[^{18}O]_2$ | $B_{40}$, 82.15 |
| $[^{13}C]_3H_8[^{18}O]O$ | $B_{41}$, 81.14 |
| $[^{13}C]_3H_8[^{18}O]_2$ | $B_{42}$, 83.16 |
| $[^{13}C]_2C[^2H]H_7[^{18}O]O$ | $B_{43}$, 81.14 |
| $[^{13}C]_2C[^2H]_2H_6[^{18}O]O$ | $B_{44}$, 82.15 |
| $[^{13}C]_2C[^2H]_3H_5[^{18}O]O$ | $B_{45}$, 83.16 |
| $[^{13}C]_2C[^2H]_4H_4[^{18}O]O$ | $B_{46}$, 84.16 |
| $[^{13}C]_2C[^2H]_5H_3[^{18}O]O$ | $B_{47}$, 85.17 |
| $[^{13}C]_2C[^2H]_6H_2[^{18}O]O$ | $B_{48}$, 86.18 |
| $[^{13}C]_2C[^2H]_7H[^{18}O]O$ | $B_{49}$, 87.19 |
| $[^{13}C]_2C[^2H]_8[^{18}O]O$ | $B_{50}$, 88.20 |
| $[^{13}C]_3[^2H]H_7[^{18}O]O$ | $B_{51}$, 82.15 |
| $[^{13}C]_3[^2H]_2H_6[^{18}O]O$ | $B_{52}$, 83.16 |
| $[^{13}C]_3[^2H]_3H_5[^{18}O]O$ | $B_{53}$, 84.16 |

TABLE 3-continued

| Species Formula | Species No., Average Enriched Mass |
|---|---|
| $[^{13}C]_3[^2H]_4H_4[^{18}O]O$ | $B_{54}$, 85.17 |
| $[^{13}C]_3[^2H]_5H_3[^{18}O]O$ | $B_{55}$, 86.18 |
| $[^{13}C]_3[^2H]_6H_2[^{18}O]O$ | $B_{56}$, 87.19 |
| $[^{13}C]_3[^2H]_7H[^{18}O]O$ | $B_{57}$, 88.20 |
| $[^{13}C]_3[^2H]_8[^{18}O]O$ | $B_{58}$, 89.21 |
| $[^{13}C]_3[^2H]H_7[^{18}O]_2$ | $B_{59}$, 84.16 |
| $[^{13}C]_3[^2H]_2H_6[^{18}O]_2$ | $B_{60}$, 86.18 |
| $[^{13}C]_3[^2H]_3H_5[^{18}O]_2$ | $B_{61}$, 88.20 |
| $[^{13}C]_3[^2H]_4H_4[^{18}O]_2$ | $B_{62}$, 90.22 |
| $[^{13}C]_3[^2H]_5H_3[^{18}O]_2$ | $B_{63}$, 92.23 |
| $[^{13}C]_3[^2H]_6H_2[^{18}O]_2$ | $B_{64}$, 94.25 |
| $[^{13}C]_3[^2H]_7H[^{18}O]_2$ | $B_{65}$, 96.27 |
| $[^{13}C]_3[^2H]_8[^{18}O]_2$ | $B_{66}$, 98.29 |

Propylene glycol exists in both the 1-2 and 1-3 isomers (referring to the carbon substituted with —OH). Tables 2 and 3 refer to the 1-2 isomers. The 1-3 isomers corresponding to the species formulae of A1-A35 and B1-B66 are also within the scope of the invention, and may be referenced as E1-E35 and F1-F66, respectively.

As to glycerol, the following species can be used as an e-cigarette solvent or tracer, wherein presently preferred species are indicated.

TABLE 4

| Species Formula | Average Enriched Mass | Species No., Comment |
|---|---|---|
| $[^{13}C]C_2H_8O_3$ | 93.10 | $C_1$ |
| $[^{13}C]_2CH_8O_3$ | 94.11 | $C_2$ |
| $[^{13}C]_3H_8O_3$ | 95.12 | $C_3$ Preferred for internal standard |
| $C_3[^2H]H_7O_3$ | 93.10 | $C_4$ |
| $C_3[^2H]_2H_6O_3$ | 94.11 | $C_5$ |
| $C_3[^2H]_3H_5O_3$ | 95.12 | $C_6$ |
| $C_3[^2H]_4H_4O_3$ | 96.12 | $C_7$ |
| $C_3[^2H]_5H_3O_3$ | 97.13 | $C_8$ |
| $C_3[^2H]_6H_2O_3$ | 98.14 | $C_9$ |
| $C_3[^2H]_7HO_3$ | 99.15 | $C_{10}$ |
| $C_3[^2H]_8O_3$ | 100.16 | $C_{11}$ |
| $[^{13}C]C_2[^2H]H_7O_3$ | 94.11 | $C_{12}$ |
| $[^{13}C]C_2[^2H]_2H_6O_3$ | 95.12 | $C_{13}$ |
| $[^{13}C]C_2[^2H]_3H_5O_3$ | 96.12 | $C_{14}$ |
| $[^{13}C]C_2[^2H]_4H_4O_3$ | 97.13 | $C_{15}$ |
| $[^{13}C]C_2[^2H]_5H_3O_3$ | 98.14 | $C_{16}$ |
| $[^{13}C]C_2[^2H]_6H_2O_3$ | 99.15 | $C_{17}$ |
| $[^{13}C]C_2[^2H]_7HO_3$ | 100.16 | $C_{18}$ |
| $[^{13}C]C_2[^2H]_8O_3$ | 101.17 | $C_{19}$ |
| $[^{13}C]_2C[^2H]H_7O_3$ | 95.12 | $C_{20}$ |
| $[^{13}C]_2C[^2H]_2H_6O_3$ | 96.12 | $C_{21}$ |
| $[^{13}C]_2C[^2H]_3H_5O_3$ | 97.13 | $C_{22}$ |
| $[^{13}C]_2C[^2H]_4H_4O_3$ | 98.14 | $C_{23}$ |
| $[^{13}C]_2C[^2H]_5H_3O_3$ | 99.15 | $C_{24}$ |
| $[^{13}C]_2C[^2H]_6H_2O_3$ | 100.16 | $C_{25}$ |
| $[^{13}C]_2C[^2H]_7HO_3$ | 101.17 | $C_{26}$ |
| $[^{13}C]_2C[^2H]_8O_3$ | 102.18 | $C_{27}$ |
| $[^{13}C]_3[^2H]H_7O_3$ | 96.12 | $C_{28}$ |
| $[^{13}C]_3[^2H]_2H_6O_3$ | 97.13 | $C_{29}$ |
| $[^{13}C]_3[^2H]_3H_5O_3$ | 98.14 | $C_{30}$, |
| $[^{13}C]_3[^2H]_4H_4O_3$ | 99.15 | $C_{31}$, |
| $[^{13}C]_3[^2H]_5H_3O_3$ | 100.16 | $C_{32}$, Preferred for standard-cig solvent |
| $[^{13}C]_3[^2H]_6H_2O_3$ | 101.17 | $C_{33}$ |
| $[^{13}C]_3[^2H]_7HO_3$ | 102.18 | $C_{34}$ |
| $[^{13}C]_3[^2H]_8O_3$ | 103.19 | $C_{35}$ |

However, the following progression of glycerol species can also be suitable for purposes of e-cigarette solvents or standards:

TABLE 5

| Species Formula | Species No., Average Enriched Mass |
|---|---|
| $[^{13}C]C_2H_8O_3$ | $D_1$, 93.10 |
| $[^{13}C]_2CH_8O_3$ | $D_2$, 94.11 |
| $[^{13}C]_3H_8O_3$ | $D_3$, 95.12 |
| $C_3[^2H]H_7O_3$ | $D_4$, 93.10 |
| $C_3[^2H]_2H_6O_3$ | $D_5$, 94.11 |
| $C_3[^2H]_3H_5O_3$ | $D_6$, 95.12 |
| $C_3[^2H]_4H_4O_3$ | $D_7$, 96.12 |
| $C_3[^2H]_5H_3O_3$ | $D_8$, 97.13 |
| $C_3[^2H]_6H_2O_3$ | $D_9$, 98.14 |
| $C_3[^2H]_7HO_3$ | $D_{10}$, 99.15 |
| $C_3[^2H]_8O_3$ | $D_{11}$, 100.16 |
| $C_3H_8[^{18}O]O_2$ | $D_{12}$, 94.11 |
| $C_3H_8[^{18}O]_2O$ | $D_{13}$, 96.12 |
| $C_3H_8[^{18}O]_3$ | $D_{14}$, 98.14 |
| $[^{13}C]C_2[^2H]H_7O_3$ | $D_{15}$, 94.11 |
| $[^{13}C]C_2[^2H]_2H_6O_3$ | $D_{16}$, 95.12 |
| $[^{13}C]C_2[^2H]_3H_5O_3$ | $D_{17}$, 96.12 |
| $[^{13}C]C_2[^2H]_4H_4O_3$ | $D_{18}$, 97.13 |
| $[^{13}C]C_2[^2H]_5H_3O_3$ | $D_{19}$, 98.14 |
| $[^{13}C]C_2[^2H]_6H_2O_3$ | $D_{20}$, 99.15 |
| $[^{13}C]C_2[^2H]_7HO_3$ | $D_{21}$, 100.16 |
| $[^{13}C]C_2[^2H]_8O_3$ | $D_{22}$, 101.17 |
| $[^{13}C]_2C[^2H]H_7O_3$ | $D_{23}$, 95.12 |
| $[^{13}C]_2C[^2H]_2H_6O_3$ | $D_{24}$, 96.12 |
| $[^{13}C]_2C[^2H]_3H_5O_3$ | $D_{25}$, 97.13 |
| $[^{13}C]_2C[^2H]_4H_4O_3$ | $D_{26}$, 98.14 |
| $[^{13}C]_2C[^2H]_5H_3O_3$ | $D_{27}$, 99.15 |
| $[^{13}C]_2C[^2H]_6H_2O_3$ | $D_{28}$, 100.16 |
| $[^{13}C]_2C[^2H]_7HO_3$ | $D_{29}$, 101.17 |
| $[^{13}C]_2C[^2H]_8O_3$ | $D_{30}$, 102.18 |
| $[^{13}C]_3[^2H]H_7O_3$ | $D_{31}$, 96.12 |
| $[^{13}C]_3[^2H]_2H_6O_3$ | $D_{32}$, 97.13 |
| $[^{13}C]_3[^2H]_3H_5O_3$ | $D_{33}$, 98.14 |
| $[^{13}C]_3[^2H]_4H_4O_3$ | $D_{34}$, 99.15 |
| $[^{13}C]_3[^2H]_5H_3O_3$ | $D_{35}$, 100.16 |
| $[^{13}C]_3[^2H]_6H_2O_3$ | $D_{36}$, 101.17 |
| $[^{13}C]_3[^2H]_7HO_3$ | $D_{37}$, 102.18 |
| $[^{13}C]_3[^2H]_8O_3$ | $D_{38}$, 103.19 |
| $[^{13}C]_2CH_8[^{18}O]O_2$ | $D_{39}$, 96.12 |
| $[^{13}C]_2CH_8[^{18}O]_2O$ | $D_{40}$, 98.14 |
| $[^{13}C]_2CH_8[^{18}O]_3$ | $D_{41}$, 100.16 |
| $[^{13}C]_2C[^2H]H_7[^{18}O]O_2$ | $D_{42}$, 97.13 |
| $[^{13}C]_2C[^2H]_2H_6[^{18}O]O_2$ | $D_{43}$, 98.14 |
| $[^{13}C]_2C[^2H]_3H_5[^{18}O]O_2$ | $D_{44}$, 99.15 |
| $[^{13}C]_2C[^2H]_4H_4[^{18}O]O_2$ | $D_{45}$, 100.16 |
| $[^{13}C]_2C[^2H]_5H_3[^{18}O]O_2$ | $D_{46}$, 101.17 |
| $[^{13}C]_2C[^2H]_6H_2[^{18}O]O_2$ | $D_{47}$, 102.18 |
| $[^{13}C]_2C[^2H]_7H[^{18}O]O_2$ | $D_{48}$, 103.19 |
| $[^{13}C]_2C[^2H]_8[^{18}O]O_2$ | $D_{49}$, 104.19 |
| $[^{13}C]_2C[^2H]H_7[^{18}O]_2O$ | $D_{50}$, 99.15 |
| $[^{13}C]_2C[^2H]_2H_6[^{18}O]_2O$ | $D_{51}$, 100.16 |
| $[^{13}C]_2C[^2H]_3H_5[^{18}O]_2O$ | $D_{52}$, 101.17 |
| $[^{13}C]_2C[^2H]_4H_4[^{18}O]_2O$ | $D_{53}$, 102.18 |
| $[^{13}C]_2C[^2H]_5H_3[^{18}O]_2O$ | $D_{54}$, 103.19 |
| $[^{13}C]_2C[^2H]_6H_2[^{18}O]_2O$ | $D_{55}$, 104.19 |
| $[^{13}C]_2C[^2H]_7H[^{18}O]_2O$ | $D_{56}$, 105.20 |
| $[^{13}C]_2C[^2H]_8[^{18}O]_2O$ | $D_{57}$, 106.21 |
| $[^{13}C]_2C[^2H]H_7[^{18}O]_3$ | $D_{58}$, 101.17 |
| $[^{13}C]_2C[^2H]_2H_6[^{18}O]_3$ | $D_{59}$, 102.18 |
| $[^{13}C]_2C[^2H]_3H_5[^{18}O]_3$ | $D_{60}$, 103.19 |
| $[^{13}C]_2C[^2H]_4H_4[^{18}O]_3$ | $D_{61}$, 104.19 |
| $[^{13}C]_2C[^2H]_5H_3[^{18}O]_3$ | $D_{62}$, 105.20 |
| $[^{13}C]_2C[^2H]_6H_2[^{18}O]_3$ | $D_{63}$, 106.21 |
| $[^{13}C]_2C[^2H]_7H[^{18}O]_3$ | $D_{64}$, 107.22 |
| $[^{13}C]_2C[^2H]_8[^{18}O]_3$ | $D_{65}$, 108.23 |
| $[^{13}C]_3[^2H]H_7[^{18}O]O_2$ | $D_{66}$, 98.14 |
| $[^{13}C]_3[^2H]_2H_6[^{18}O]O_2$ | $D_{67}$, 99.15 |
| $[^{13}C]_3[^2H]_3H_5[^{18}O]O_2$ | $D_{68}$, 100.16 |
| $[^{13}C]_3[^2H]_4H_4[^{18}O]O_2$ | $D_{69}$, 101.17 |
| $[^{13}C]_3[^2H]_5H_3[^{18}O]O_2$ | $D_{70}$, 102.18 |
| $[^{13}C]_3[^2H]_6H_2[^{18}O]O_2$ | $D_{71}$, 103.19 |
| $[^{13}C]_3[^2H]_7H[^{18}O]O_2$ | $D_{72}$, 104.19 |
| $[^{13}C]_3[^2H]_8[^{18}O]O_2$ | $D_{73}$, 105.20 |
| $[^{13}C]_3[^2H]H_7[^{18}O]_2O$ | $D_{74}$, 100.16 |
| $[^{13}C]_3[^2H]_2H_6[^{18}O]_2O$ | $D_{75}$, 101.17 |
| $[^{13}C]_3[^2H]_3H_5[^{18}O]_2O$ | $D_{76}$, 102.18 |
| $[^{13}C]_3[^2H]_4H_4[^{18}O]_2O$ | $D_{77}$, 103.19 |
| $[^{13}C]_3[^2H]_5H_3[^{18}O]_2O$ | $D_{78}$, 104.19 |
| $[^{13}C]_3[^2H]_6H_2[^{18}O]_2O$ | $D_{79}$, 105.20 |
| $[^{13}C]_3[^2H]_7H[^{18}O]_2O$ | $D_{80}$, 106.21 |
| $[^{13}C]_3[^2H]_8[^{18}O]_2O$ | $D_{81}$, 107.22 |
| $[^{13}C]_3[^2H]H_7[^{18}O]_3$ | $D_{82}$, 102.18 |
| $[^{13}C]_3[^2H]_2H_6[^{18}O]_3$ | $D_{83}$, 103.19 |
| $[^{13}C]_3[^2H]_3H_5[^{18}O]_3$ | $D_{84}$, 104.19 |
| $[^{13}C]_3[^2H]_4H_4[^{18}O]_3$ | $D_{85}$, 105.20 |
| $[^{13}C]_3[^2H]_5H_3[^{18}O]_3$ | $D_{86}$, 106.21 |
| $[^{13}C]_3[^2H]_6H_2[^{18}O]_3$ | $D_{87}$, 107.22 |
| $[^{13}C]_3[^2H]_7H[^{18}O]_3$ | $D_{88}$, 108.23 |
| $[^{13}C]_3[^2H]_8[^{18}O]_3$ | $D_{89}$, 109.24 |

Example 1: Synthesis of an Isotopically-Labeled Propylene Glycol Species

Species A3 above was synthesized according to the following scheme.

To a suspension of Reactant 1 (lithium aluminum hydride) (625 mg, 16.48 mmol) in (tetrahydrofuran ("THF"), (15 ml) was added a solution of Reactant 2 (2-oxopropanoic acid-$^{13}C_3$, from Sigma Aldrich, St. Louis, Mo.) (500 mg, 5.49 mmol) in THF (5 mL) drop-wise over ~5 mins. Since the reaction is exothermic, bubbling was observed, as expected. The reaction was then stirred at room temperature for 2 h. Reaction progress was monitored by Thin Layer Chromatography ("TLC"). Diethyl ether (Et2O) showed a faint spot when stained with phosphomolybidic acid ("PMA") at retention factor ("Rf") 0.25.

0.646 mL water, 0.646 mL 15% NaOH (aq) then 1.9 mL water were added cautiously. The solids were filtered off, rinsing with ethyl acetate ("EtOAc"). Solvents were removed in vacuo to give desired product >90% pure with some residual EtOAc. 220 mg.

The material was purified by silica gel plug eluting with 19:1 DCM (dichloromethane ("DCM")/methanol ("MeOH") (loaded with DCM, used thinnest, tall funnel). Product came off cleanly in fractions 3 and 4, stained with PMA, Rf 0.2 in 19:1 DCM/MeOH. The final product was at a purity of 96.6 wt. % (966 μg/mg). Electrospray MS(ES+) m/z 102.1 (M+Na)⁺.

Table 6 provides the normalized isotopic mass distribution, including the naturally occurring higher isotopic masses.

TABLE 6

| Abundance | m/z |
|---|---|
| Undetected | 99.1 (Unlabeled + Na) |
| Undetected | 100.1 (+)(+1 + Na) |
| 3.8 | 101.2 (+2 + Na) |
| 100 | 102.1 (+3 + Na) |

Mass Spectrometry Methods

The following describes the equipment, equipment settings and conditions used to obtain the LC-MS/MS data.

Waters ACQUITY UPLC® Binary Solvent Manager

Mobile Phase A: 5:95:1 ACN:H2O:HCOOH

Mobile Phase B: 95:5:1 ACN:H2O:HCOOH

Table 7 reflects the gradient program.

TABLE 7

| Steps | Total time (min) | Time interval (min) | MPH A% | Flow rate (mL/min) | Curve |
|---|---|---|---|---|---|
| 1 | 0.00 | — | 52 | 0.8 | — |
| 2 | 0.10 | 0.10 | 52 | 0.8 | 6 |
| 3 | 1.36 | 1.26 | 46 | 0.8 | 6 |
| 4 | 1.37 | 0.01 | 20 | 0.8 | 6 |
| 5 | 1.45 | 0.08 | 20 | 0.8 | 6 |
| 6 | 1.46 | 0.01 | 52 | 0.8 | 6 |

Precolumn: Waters, Frit Assembly, stainless steel replacement filters, 2.1 mm, 0.2 µm, Part No.: 700002775.

Analytic Column: Waters, CORTECS™ UPLC® C18+, 90 Å, 50×2.1 mm, 1.6 µm, Part No.: 186007114, Temperature: 45° C.

Autosampler: Waters ACQUITY UPLC® Sample Manager, Temperature: 4° C.

Table 8 provides the most pertinent details of the detector (AB SCIEX API 4000®).

TABLE 8

| MS/MS# | S/N | Horizontal position* | Vertical position* | Injection volume (µL)* |
|---|---|---|---|---|
| EQ-LNK-MS-0041 | V242 0308 | 6 | 10 | 3 |
| EQ-LNK-MS-0034 | V00 50211 | 5 | 10 | 10 |
| EQ-LNK-MS-0035 | V05 00301 | 3 | 10 | 10 |
| EQ-LNK-MS-0038 | S137 0211 | 3 | 10 | 3 |

Table 9 provides the most pertinent details of the acquisition method.

TABLE 9

| Species | Precursor ion m/z | | Product ion m/z | Dwell time (msec) |
|---|---|---|---|---|
| Propylene Glycol: | 285.0 | → | 163.2 | 10 |
| $^{13}C_3$-Propylene Glycol: | 288.2 | → | 166.3 | 130 |
| $^{13}C_3$-$d_3$-Propylene Glycol (IS): | 291.2 | → | 169.3 | 65 |

The m/z listed above may vary by 0.5 amu from what is used with the current calibration due to unit resolution of quadrupole mass spectrometers. Instrument parameters contained in the method file may need to be adjusted from instrument to instrument.

Further pertinent details of the mass spectrometry method used are provided in Table 10.

TABLE 10

| Source | Turbo Spray (ESI) |
|---|---|
| Ion Mode | Positive |
| Acquisition Time | 1.6 minutes |
| Software Version | Analyst 1.6.2 |
| Source Temperature | 300.0° C. |
| Resolution $Q_1$ | Unit |
| Resolution $Q_3$ | Unit |
| Curtain Gas | 40.00 |
| $GS_1$ | 60.00 |
| $GS_2$ | 65.00 |
| IonSource Voltage | 5500.00 |
| Collision Gas | 10.00 |
| Declustering Potential | 33.00 |
| Entrance Potential | 5.00 |
| Collision Energy | 11.00 |
| Exit Potential | 10.00 |

The above example of the synthesis and purification of the A3 species is representative of procedures regarding other species of 1-2 propylene glycol. For each species, the selection of the Reactant 2 starting material having the desired isotopic moieties (e.g., $^2H$) would be required. For 1-3 propylene glycol species, one would start with 3-oxopropanoic acid-$^{13}C_3$ instead of 2-oxopropanoic acid-$^{13}C_3$. Procedures for the synthesis of glycerol species would also require the selection of the appropriate starting material (e.g., 2,3-oxopropanoic acid-$^{13}C_3$). To synthesize some species, it would be necessary to achieve a reduction of carbon-carbon double bonds with $^2H$ using a catalyst such as platinum or palladium. One of skill in the art would be able to carry out these procedures in light of the teachings of Example 1.

Purified forms of the isotopically-labeled species of propylene glycol and glycerol are also within the scope of the present invention. The term "purified forms" as used herein shall mean the isotopically-labeled species of propylene glycol and glycerol that are present in a purity of at least 95 wt. %, preferably at least 96 wt. % and more preferably at least 98 wt. %. Any purification method that results in these purities is within the scope of the inventive purified forms.

Methods of Testing eCigarettes

The method includes combining a biological sample containing an undetermined quantity of labeled species delivered by the e-cigarette as described herein with a known quantity of an internal standard to discover the undetermined quantity of the labeled species. Sample preparation and processing techniques for the analysis of isotopically-labeled propylene glycol and/or glycerol species in biological samples to which a second isotopically-labeled species of propylene glycol or glycerol has been added as internal standard can include, but are not limited to:

Protein precipitation with acid, including but not limited to:
Perchloric acid
Trichloroacetic acid
Phosphoric acid
Hydrochloric acid
Trifluoroacetic acid Protein precipitation with organic solvent, including but not limited to:
Methanol
Acetonitrile
Acetone
Ethanol
Propanol/Isopropanol Liquid-liquid extraction with organic solvent following dilution of the matrix with or without altering the native plasma pH:

Ethyl Acetate
Methyl t-butyl ether
n-Butyl chloride
Mixtures of solvents including hexanes, pentanes, alcohols, ethers, ketones, or alkyl halides Solid-phase extraction with sorbent materials including, but not limited to the following techniques. A summary of some of these and other suitable techniques was annexed to 61/875,647 and 61/875,650 as Appendices, which are incorporated by reference herein in their entireties for any purpose whatsoever.

Silica
Polymeric polystyrene divinyl benzene (modified or unmodified)
C2, C4, C8, C18
Diol
Phenyl boronic acid Propylene glycol and glycerol (or their derivatives) may be further separated from co-extracted matrix components by chromatographic or electrophoretic techniques that exploit minor differences in polarity such as:

Gas Chromatography (GC)
High-performance liquid chromatography ("HPLC")
Ultra High-performance liquid chromatography ("UH-PLC")
Capillary Electrophoresis ("CE")

Detection of propylene glycol and glycerol in extracts from biological samples may be performed with or without derivatization of the analytes by mass spectrometry, including but not limited to:

Quadrupole Mass Spectrometer
Triple quadrupole Mass Spectrometer
Time-of-flight Mass Spectrometer
With ionization by, but not limited to:
Atmospheric-pressure chemical ionization ("APCI")
Electrospray Ionization ("ESI")
Matrix-assisted laser desorption/ionization (MALDI)

The applicable ionization and fragmentation parameters of the mass spectrometer can include, but are not limited to:

Polarity
Gas flows
Ionization source temperature
Ionization voltage
Lens and coil voltages
Declustering potential
Collision energy
Exit potential These parameters can be adjusted to detect the specific isotope-labeled form of propylene glycol or glycerol used as the solvent in the e-cigarette and for the specific isotope-labeled species of propylene glycol or glycerol (or their derivatives) used as the internal standard.

In accordance with further aspects of the disclosure, a pre-determined quantity of isotopically-labeled solvent is disposed in an e-cigarette or cartridge thereof to provide a predetermined dose to the user. Preferably, all, or nearly all, of the solvent in the e-cigarette is isotopically-labeled solvent. The predetermined quantity can be, for example, between about 0.001 grams and about 3.0 grams, between about 0.05 grams and about 2.0 grams, between about 0.1 grams and about 1.0 gram, between about 0.2 grams and about 0.8 grams, or any increment between any of the aforementioned ranges of about 0.001 gram. In some embodiments, the predetermined quantity can be between about 1.0 ml and 2.0 ml, such as about 1.0 ml, about 1.1 ml, about 1.2 ml, about 1.3 ml, about 1.4 ml, about 1.5 ml, about 1.6 ml, about 1.7 ml, about 1.8 ml, about 1.9 ml and about 2.0 ml. The cartridge can be in any suitable form, as known in the art, including a sidewall for containing the predetermined quantity of isotopically-labeled solvent (and nicotine, as appropriate), and if desired, an exit port for permitting the solvent to egress the container.

In the e-cigarette cartridge, the concentration of nicotine in the isotopically-labeled solvent is preferably between about 1.4 and about 2.2 v.v %, and more preferably between about 1.6 and about 2.0 v/v %. In some preferred embodiments, the concentration of nicotine in the isotopically-labeled solvent is about 1.8 v/v %.

Any of the isotopically solvents disclosed herein and listed in the above tables, including species A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, B1, B2, B3, B4, B5, B6, B7, B8, B9, B10, B11, B12, B13, B14, B15, B16, B17, B18, B19, B20, B21, B22, B23, B24, B25, B26, B27, B28, B29, B30, B31, B32, B33, B34, B35, B36, B37, B38, B39, B40, B41, B42, B43, B44, B45, B46, B47, B48, B49, B50, B51, B52, B53, B54, B55, B56, B57, B58, B59, B60, B61, B62, B63, B64, B65, B66, C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, D1, D2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34, D35, D36, D37, D38, D39, D40, D41, D42, D43, D44, D45, D46, D47, D48, D49, D50, D51, D52, D53, D54, D55, D56, D57, D58, D59, D60, D61, D62, D63, D64, D65, D66, D67, D68, D69, D70, D71, D72, D73, D74, D75, D76, D77, D78, D79, D80, D81, D82, D83, D84, D85, D86, D87, D88 or D89 alone, or in combination with nicotine, can be provided inside of a cartridge whether the cartridge is replaceable or integral with the e-cigarette, and whether or not nicotine is included in the cartridge. Moreover, two or more of the aforementioned solvents can be combined in the cartridge if desired, alone and/or with nicotine and/or other solvents or materials.

Preferred embodiments include the use of species A3 as the solvent, and any of species A29-A33 as the internal standard. Further preferred embodiments include the use of species C3 as the solvent, and any of species C29-C32 as the internal standard.

In accordance with a further aspect of the disclosure, a method of determining the quantity of a compound delivered to a user of an e-cigarette is provided. The method includes providing a user with an e-cigarette that is loaded with a predetermined quantity of an isotopically-labeled solvent. In preferred embodiments, all, or nearly all, of the solvent in the e-cigarette is isotopically-labeled solvent. The isotopically-labeled solvent may include nicotine. If desired, the solvent and/or nicotine may be provided in the form of a replaceable cartridge. The method can further include dosing the user with the e-cigarette. A fluid sample can then be obtained from the user, such as a sample of blood, urine, and/or saliva. The fluid sample can then be measured to determine the levels of unlabeled (if present) and isotopically-labeled species of the labeled solvent, or derivative compound of such analyte in the fluid using any suitable technique as described herein, such as mass spectrometry. For example, a derivative compound can be made by reacting one or more of the analytes to make them more amenable to a detection method, such as by introducing a nitrogen or carboxylic acid group that is more easily ionized than an alcohol or hydroxyl group. Where blood is used as the fluid, the plasma of the blood can be tested for such compounds.

The method yet further can include determining the level of said compound in the fluid that was delivered by the e-cigarette based on measured levels of unlabeled and isotopically-labeled species of said compound in the blood plasma. Determining the levels of the compounds (e.g., solvent) can be aided by adding a standard to the fluid prior to testing, wherein the standard represents a second predetermined amount of the same or different isotopically-labeled solvent. The solvent can be any of the solvents disclosed herein.

As referred to herein, the term e-cigarette cartridge can include any container (e.g., capsule) suitable for disposition into an e-cigarette and suitable for containing a liquid that can be vaporized to deliver an isotopically-labeled solvent that preferably includes nicotine to a user. The cartridge can be of any desired physical format, as known in the art. Alternatively, an e-cigarette can be provided wherein a predetermined quantity of isotopically-labeled solvent is disposed in the e-cigarette prior to testing into a chamber within the e-cigarette for delivery to the user.

In further accordance with the disclosure, a method is provided of determining a first quantity of a compound exogenously introduced to an animal where the compound occurs endogenously in the blood plasma of the animal in a second quantity (whether through food, metabolism or expression). The method includes dosing the animal with a predetermined quantity of an isotopically-labeled species of the compound, drawing a fluid (e.g., saliva, urine, and/or blood) sample from the animal, measuring the fluid levels of unlabeled and isotopically-labeled species of the compound in the fluid from the fluid sample, such as by using mass spectrometry, and determining the level of the compound in the fluid that was delivered by the dosing based on measured levels of unlabeled and isotopically-labeled species of the compound in the fluid. The animal can be a human, or other animal. Dosing may be accomplished via oral, buccal, suppository and/or transdermal techniques.

In some embodiments, when drawing blood as a bodily fluid for analysis in accordance with the method recited immediately above, it can be desirable to draw it at or near $t_{max}$, which refers to the time period post-dosing that corresponds to $C_{max}$. In turn, $C_{max}$ refers to the peak plasma concentration of a dosed compound vs. time since dosing. However, it can be difficult to draw blood at $t_{max}$ so one can draw the blood at a time near $t_{max}$ when the concentration is relatively near $C_{max}$. In some implementations the blood is preferably drawn within five, ten, fifteen, twenty, twenty five, or thirty minutes of $t_{max}$. In accordance with further implementations, blood can be drawn 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90 minutes, or any other desired time increment after the subject is first dosed.

Example 2: Clinical Study

A clinical study protocol was generated. The objectives of this study were to measure C13-labeled PG in blood and to evaluate the extent of second-hand exposure to PG and nicotine during use of a commercially-available electronic nicotine delivery system (vaporizer).

This was an open-label, single-center study that included three consumers of a commercially available nicotine vaporizer ("vaping" group) and three "nicotine-free" subjects who did not use nicotine-containing products of any kind for 14 days prior to the Test Visit. All subjects completed screening procedures and checked in to the clinic on the morning of the Test Visit. All subjects remained in the clinic until the completion of the final study procedure later that day.

Following completion of check-in procedures, all subjects were seated in a room together approximately 30 minutes prior to the start of product administration. Subjects in the vaping group began using the vaporizers as directed by the clinic staff—one inhalation at least 3 seconds in duration every 30 seconds for a total of 30 inhalations. Each vaporizer contained a 1.8 v/v % nicotine solution in a PG vehicle. All subjects remained in the product administration room for 2 hours following the start of product administration. Approximately 4 hours following the start of product administration subjects were provided a meal high in PG content. Blood samples were collected approximately 10 minutes prior to the start of, and approximately 2.5, 10, 15, 20, 30, 45, 60, 120, 240, 270, 300, 360, and 480 minutes after start of product administration in order to assess concentrations of labeled and unlabeled PG and nicotine.

The following investigational products were used:
Vaporizer: KGo bottom-feeder tank with a single coil (2.4 ohm resistance), 1100 mAh rechargeable battery (3.4 volts) (GNS Vapor, Lincoln, Nebr.)
Nicotine Solution: 99.9% pharmaceutical grade nicotine (Nicobrand, Coleraine, UK)
C13-labeled PG: Propyleneglycol-$^{13}C_3$, 96.8 wt. % pure (Aptochem, Montréal, QC, Canada)

The nicotine solution was diluted to a final concentration of 1.8 v/v % in the C13-labeled PG. Approximately 1 mL or less of the nicotine-PG solution was loaded into the vaporizer tank on the morning of the Test Visit.

Except as required by the study, consumption of tobacco- or nicotine-containing products was not permitted from check-in through discharge from the clinic.

Each vaping subject completed 30 inhalations from the vaporizer, with each inhalation at least 3 seconds in duration at 30-second intervals. The clinic staff documented the start and stop time of the product administration and indicated to the subjects when to start each inhalation.

All subjects remained in the product administration room for 2 hours following the start of product administration.

Subjects had fasted for at least 2 hours prior to product administration. A meal containing common foods that are regarded as high in PG content (e.g., 1 Big Mac, small salad with 3 oz Kraft Free Ranch Salad Dressing, 2 chocolate fudge Pop Tarts, 12 oz A&W Root Beer, or similar) was served to each subject approximately 4 hours following the start of product administration. Subjects consumed the entire meal within ~30 minutes. No other food was allowed until after the last blood sample was taken.

Pharmacokinetic (PK) blood samples for plasma nicotine analysis were taken by direct venipuncture into a 6 mL plastic $K_2$ EDTA (lavender top) vacutainer tube. Approximately 90 mL of blood was collected at a time. As appropriate, product use continued during blood draws.

The samples were kept at room temperature prior to centrifuge, and were centrifuged at 2500 RPM for 15 minutes at 4° C. within 60 minutes of collection. After centrifugation, the plasma was transferred to two methanol-prewashed polypropylene screw cap tubes, properly labeled, and then stored at −20° C. (+/−10° C.) or below (within 90 minutes from collection) until analyzed by Celerion Bioanalytical Services. The pipette used to transfer the plasma was prewashed with methanol.

Plasma PG (labeled and unlabeled) and nicotine were analyzed by LC-MS/MS using analytical methods with appropriate quality controls in accordance with FDA Good Laboratory Practice (GLP) regulations (Title 21 CFR Part 58). The LC-MS/MS instrument used was model API 4000™, supplied by AB SCIEX (Framingham, Mass.). The internal standard used for the LC-MS/MS was propylene glycol-$^{13}C_3{}^2H_3$ ($^{13}C_3{}^2H_3H_5O_2$), species A30. The details of the LC-MS/MS methods were generally in accordance with those as described above.

Clinical Trial Results

Figure 1:
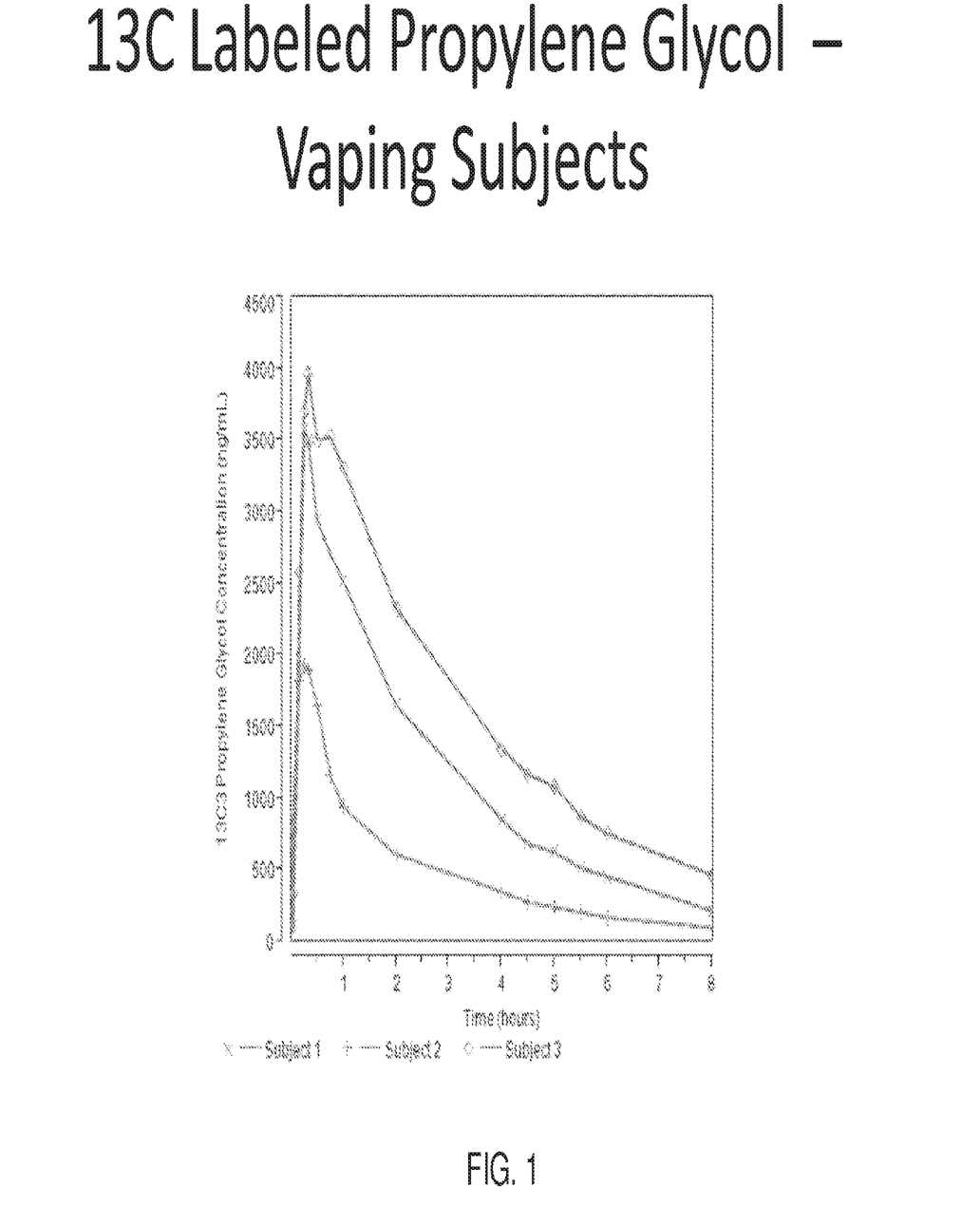
FIG. 1 displays the blood concentration of labeled propylene glycol vs. time profile for the vaping subjects, Subjects 1-3.
Figure 2:
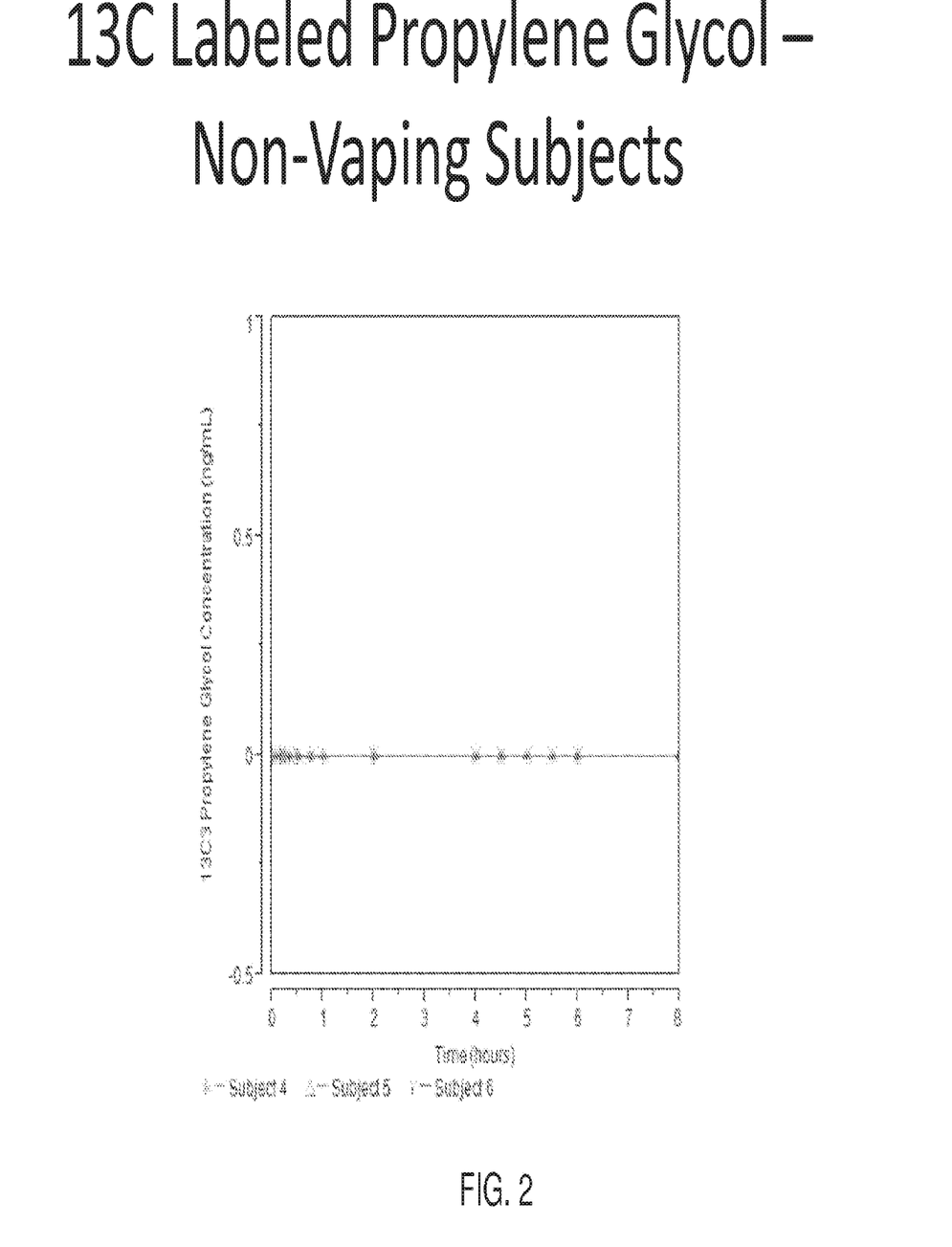
FIG. 2 displays the blood concentration of labeled propylene glycol vs. time profile for the non-vaping subjects, Subjects 4-6.
Figure 3:
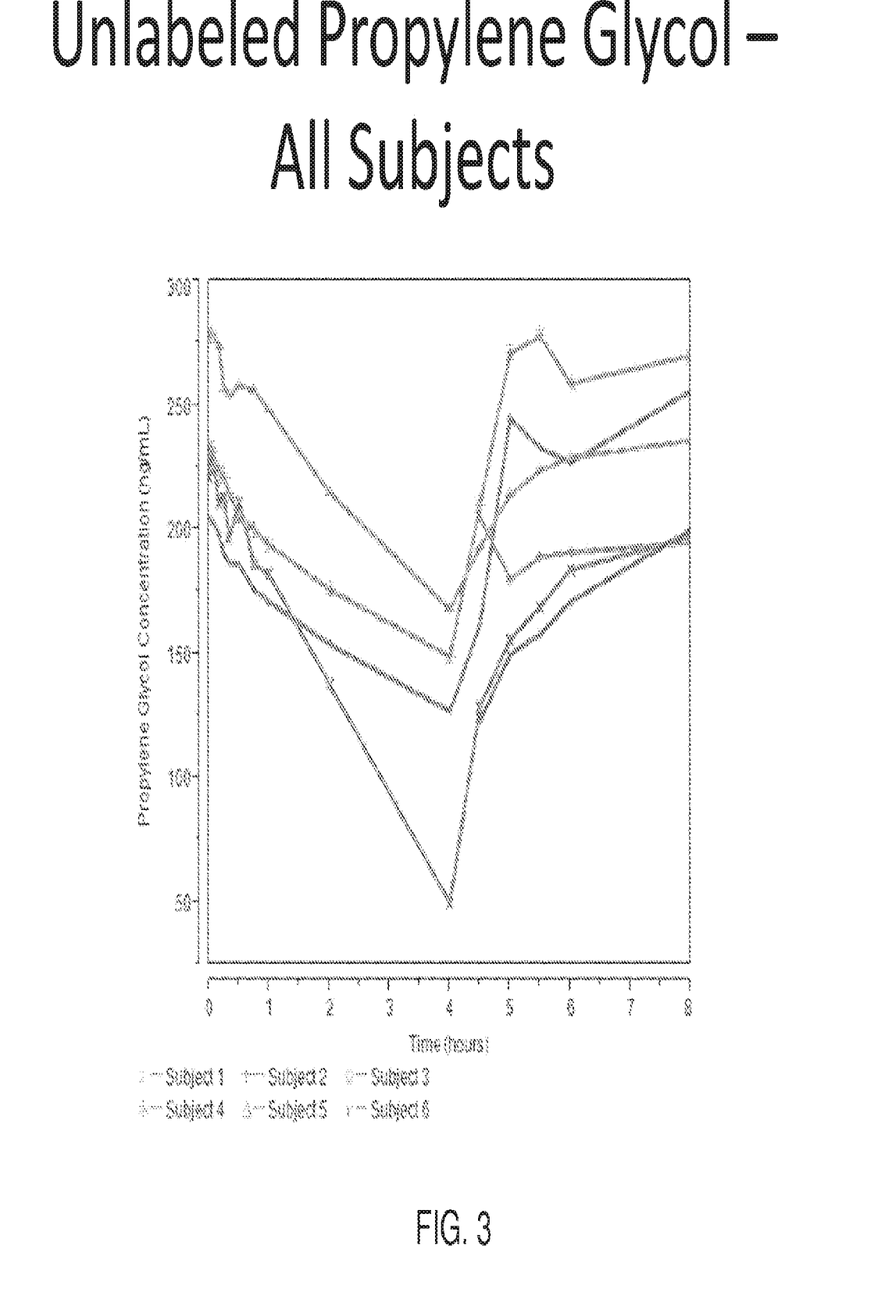
FIG. 3 displays the blood concentration of unlabeled propylene glycol vs. time profile for all subjects, Subjects 1-6. The meal was ingested by subjects at 4 hours, causing the concentrations of unlabeled propylene glycol to increase.

The LC-MS/MS analysis resulted in a blood plasma concentration measurement at each sample time point. The resulting blood concentrations of labeled propylene glycol ($[^{13}C]_3H_8O_2$, A3) vs. time profiles for each of the six subjects were tabulated. FIG. 1 displays the blood concentration of labeled propylene glycol vs. time profile for the vaping subjects, Subjects 1-3. FIG. 2 displays the blood concentration of labeled propylene glycol vs. time profile for the non-vaping subjects, Subjects 4-6. As expected, the non-vaping subjects had essentially no detectable levels of labeled propylene glycol. FIG. 3 displays the blood concentration of unlabeled propylene glycol vs. time profile for all subjects, Subjects 1-6. The stark contrast between the profiles for the vaping subjects (FIG. 1) and non-vaping subjects (FIG. 2) validates the overall efficacy of using isotopically-labeled propylene glycol ($[^{13}C]_3H_8O_2$, A3) to determine the amount of solvent delivered by an e-cigarette. The magnitudes of the values plotted on FIG. 3 show that exogenous levels of unlabeled propylene glycol are significant, and that isotopic labeling may be necessary to determine the quantity of exogenous propylene glycol introduced by an e-cigarette.

In alternate embodiments, the clinical trial is run with a total of 12-24 patients. In further alternate embodiments, the trials are run to measure the quantities of formaldehyde and/or acetaldehyde delivered by the e-cigarette, either with or without determination of the quantity of solvent delivered by the e-cigarette.

The embodiments heretofore described have been in the context of determining the amount of exogenous solvent delivered via electronic nicotine delivery systems by means of an isotopically labeled species of that solvent. However, those of skill in the art will appreciate that the methods herein taught will have applications outside of this context. Therefore, in some embodiments, the invention is directed to methods regarding nicotine delivery systems that heat a solvent by nonelectronic means, e.g., by exothermic reaction. Some embodiments are directed to methods regarding the delivery of therapeutic drug substances delivered as vaporized solutions, or mists or dispersions. As used herein, the term "therapeutic drug substance" means the active pharmaceutical ingredient (e.g., new molecular entity) in a drug product that has been approved by a pharmaceutical marketing authority (e.g., FDA).

The methods, systems, and articles of the present disclosure, as described herein, among other things, provide for improved techniques for diagnostic measurement of the effects of intake of exogenous compounds, such as those from electronic cigarettes. It will be apparent to those skilled in the art that various modifications and variations can be made in the devices, methods, and articles of the present disclosure without departing from the spirit or scope of the disclosure. Thus, it is intended that the present disclosure include modifications and variations that are within the scope of the subject disclosure and equivalents. The detailed descriptions of the methods used here, including the test protocol and LC-MS/MS analysis, are intended to provide illustrative examples, and not to limit the scope of the invention.

What is claimed is:

1. A method of determining a quantity of a compound delivered to a user of an e-cigarette comprising:
   providing a user with an e-cigarette including an e-cigarette cartridge loaded with a liquid that includes a predetermined quantity of solvent that includes non-radioactive isotopically labeled propylene glycol that is isotopically enriched by at least three atomic mass units;
   dosing the user with said e-cigarette;
   obtaining a bodily fluid sample from the user; and
   determining the amount of isotopically-labeled propylene glycol in the bodily fluid by measuring the concentration of isotopically-labeled propylene glycol in the bodily fluid sample.

2. The method according to claim 1, wherein said liquid further comprises nicotine.

3. The method according to claim 2, wherein the concentration of said nicotine in said liquid is between about 0.3 and about 4.0 v/v %.

4. The method of claim 1, wherein the bodily fluid sample is a blood sample.

5. The method of claim 4, wherein the level of isotopically-labeled propylene glycol in a blood plasma portion of the blood sample is measured using mass spectrometry.

6. The method of claim 1, wherein the bodily fluid sample is a saliva sample.

7. The method of claim 6, wherein the level of isotopically-labeled propylene glycol in the saliva sample is measured using mass spectrometry.

8. The method of claim 1, wherein the bodily fluid sample is a urine sample.

9. The method of claim 8, wherein the level of isotopically-labeled propylene glycol in the urine sample is measured using mass spectrometry.

10. The method of claim 1, wherein only the carbon atoms of the propylene glycol are isotopically weighted.

11. The method of claim 1, wherein only the hydrogen atoms of the propylene glycol are isotopically weighted.

12. The method of claim 1, wherein only the hydrogen atoms and oxygen atoms of the propylene glycol are isotopically weighted.

13. The method of claim 1, wherein the carbon atoms, hydrogen atoms and carbon atoms of the propylene glycol are each isotopically weighted.

14. The method of claim 1, wherein only the carbon atoms and oxygen atoms of the propylene glycol are isotopically weighted.

15. The method of claim 1, wherein only the hydrogen atoms and carbon atoms of the propylene glycol are isotopically weighted.

16. An e-cigarette loaded with a mixture including propylene glycol that is isotopically enriched by at least three atomic mass units.

17. The e-cigarette of claim 16, wherein the mixture further includes nicotine.

18. The e-cigarette of claim 17, wherein the concentration of said nicotine in said mixture is between about 0.3 and about 4.0 v/v %.

19. A cartridge for an e-cigarette wherein the cartridge is loaded with a mixture including propylene glycol that is isotopically enriched by at least three atomic mass units.

* * * * *